United States Patent [19]
Collu et al.

[11] Patent Number: 5,824,516
[45] Date of Patent: Oct. 20, 1998

[54] INTERNAL STANDARDS FOR QUANTITATIVE COMPETITIVE PCR

[75] Inventors: Robert Collu; JianQing Tang, both of Montréal; Ginette Lagacé, Boucherville, all of Canada

[73] Assignee: Centre de Recherche de l'Hôpital Ste-Justine, Montréal, Canada

[21] Appl. No.: 736,724

[22] Filed: Oct. 25, 1996

Related U.S. Application Data

[60] Provisional application No. 60/008,012 Oct. 27, 1995.
[51] Int. Cl.$^6$ .......................... C12P 19/34; C07H 21/04; C07H 21/02; C07H 21/00
[52] U.S. Cl. ....................... 435/91.2; 536/22.1; 536/25.3; 435/91.1
[58] Field of Search ................................. 536/22.1, 25.3; 435/91.2, 91.1

[56] References Cited

U.S. PATENT DOCUMENTS 5,219,727  6/1993  Wang ........................................... 435/6

OTHER PUBLICATIONS

Sidhu et al. Competitor internal standards for quantitative detection of mycoplasma DNA, vol. 128, pp. 207–212, 1995.

Li, H.H. et al., 1988, *Nature*, 335:414–417.
Rappolee, D.A., et al., 1988, *Science* 241:708–712.
Gilliland, G. et al., 1990, *Proc. Natl. Acad. Sci. USA*, 87:2725–2729.
Forster E., 1994, *BioTechnique*, 16(1):18–20.

*Primary Examiner*—Kenneth R. Horlick
*Assistant Examiner*—Joyce Tung
*Attorney, Agent, or Firm*—Swabey Ogilvy Renault France; Côté

[57] ABSTRACT

The present invention relates to a method for constructing internal standards used in competitive polymerase chain reaction (PCR) for determining the amount of a target nucleic acid sequence in a sample. The method comprises the steps of a) digesting the cloned target nucleic acid sequence with a cohesive-end generating restriction endonuclease; b) filling the restriction endonuclease cohesive-ends of step a) by Klenow fragment of DNA polymerase; and c) blunt-end ligating the fragment of nucleic acid of step b) to form the internal standard. The internal standard nucleic acid sequence differs from the target nucleic acid sequence such that a restriction endonuclease recognition site is destroyed by adding sufficient contiguous bases to the target nucleic acid sequence such that the size difference between the target nucleic acid sequence and the internal standard nucleic acid sequence can be detected by gel electrophoresis.

5 Claims, 4 Drawing Sheets

- ▲ Primers used for competitive PCR
- ▰▰▰ Insert DNA for the construction of internal standard
- ◡ Plasmid sequence
- ▭ Unique restriction endonuclease cut-site

INTERNAL STANDARDS FOR QUANTITATIVE COMPETITIVE PCR

This application claims the benefit of U.S. Provisional application No. 60/008,012 filed on Oct. 27, 1995.

BACKGROUND OF THE INVENTION (a) Field of the Invention

The invention relates to a method of constructing internal standards for accurately quantitating levels of specific RNA and DNA species by competitive polymerase chain reaction techniques.

(b) Description of Prior Art

DNA and RNA have been quantitated for long time using their absorbance at 260 nm wave length of ultra-violet light. This method has a sensitivity in the order of micrograms and is therefore unsuitable when nanograms or even picograms of DNA/mRNA need to be assayed in studies using the tools of modern molecular biology.

The development of the PCR technique has made it possible to amplify a single copy of a molecule (Li, H. H. et al., 1988, *Nature*, 335:414–417), and this technique is thus a very sensitive tool to be used to assay very small amounts of sample.

The polymerase chain reaction requires the use of oligonucleotide primers complementary to sequences flanking a particular region of interest for primer-directed DNA synthesis in opposite and overlapping directions. With repeated cycles of high-temperature template denaturation, oligonucleotide primer reannealing, and polymerase-mediated extension, DNA sequences can be faithfully amplified several hundred-thousand fold.

Generally PCR requires knowledge of the sequence of both the 5' and the 3' end of the template being amplified so that two different primers for each template may be designed, one primer for the sense strand and one primer for the antisense strand.

In theory, only one copy of the target gene need be present in a sample for the polymerase chain reaction to adequately target and amplify it. For example, the polymerase chain reaction amplification technique has been used to analyze the DNA in an individual diploid cell and a single sperm (Li, H. et al., *Nature* 335:414–417 (1988)).

Although it has been possible to detect and amplify large amounts of rare DNA or mRNA transcripts, it has been more difficult to quantitate the amount of the nucleic acid species in the starting material for, although PCR can detect the presence of a targeted nucleic acid species in the starting material, the results of conventional PCR cannot be used to calculate the pre-amplification levels of that targeted nucleic acid. This has precluded the use of PCR in many situations, for example, in an analysis of the fold induction of a specific mRNA in response to exogenous stimuli.

The main constraint in obtaining quantitative data from conventional PCR is inherent in the amplification process. Because amplification is (at least initially) an exponential process, small differences in any of the variables which control reaction rate will dramatically affect the yield of PCR product. Variables which influence the rate of the PCR reaction include the concentrations of polymerase, deoxynucleoside triphosphate substrates (dNTP's), $Mg^{++}$, target DNA and primers; annealing, extension and denaturing temperatures; cycle length and cycle number; the rate at which the temperature is changed from one step to another within each amplification cycle; rate of "primer-dimer" formation; and presence of contaminating DNA.

Further, even when these parameters are controlled precisely, there is tube-to-tube variation which precludes accurate quantitation. For example, significant differences in yield occur in PCR samples which are prepared as a pool and then aliquoted into separate tubes and amplified in the same run. The basis for this variation is not certain—it may be related to events which occur during the first few cycles, or small temperature variances across the thermal cycler block.

Methods have been described for quantitating cDNA species by PCR, usually by co-amplifying a second, unrelated template (Rappolee, D. A., et al., *Science* 241:708–712 (1988)). These methods are critically dependent on several variables, including cycle number and amount of starting mRNA of each species. Even when these variables are adequately controlled, it is unlikely that the unrelated control template will be amplified at precisely the same rate as the unknown template. Small differences in the rate of amplification of the two templates are magnified during PCR and may grossly over- or underestimate the amount of the unknown template present.

Among the methods described for the assay of DNA and mRNA quantities, competitive PCR is a reasonable choice (Gililand, G. et al., 1990, *Proc. Natl. Acad. Sci.* USA, 87:2725–2729). The principle of the method is that a target is amplified by PCR in the presence of a competitor. The target is the DNA/cDNA to be measured and the competitor is the target modified by the removal of a single restriction endonuclease site. Since the competitor has the same sequence as the target except for the modification of a restriction site, the final products amplified from the target and the competitor are distinguishable by digestion with the appropriate restriction endonuclease. By titrating an unknown amount of target against a serial dilution of known amounts of the corresponding competitor, the amount of the target can be reliably and reproducibly quantitated. Since this method uses the same primers for an identical sequence of the target and of the competitor (except for the modifications introduced to remove the restriction site concerned), unevenness of amplification can be reduced to a minimum.

Mutagenesis of the cloned target has been originally proposed to remove the selected restriction site (Gililand, G. et al., 1990, *Proc. Natl. Acad. Sci.* USA, 87:2725–2729). More recently, a PCR-based construction of competitor has also been proposed (Forster E., 1994, *BioTechnique*, 16(1):18–20). However, these procedures usually require a few working days or several runs of PCR and need special materials such as primers.

Taking advantage that many restriction endonucleases recognize and cut a short specific sequence and release protruding termini, here we propose a simple method for the construction of competitors which takes little time and eliminates the need of special primers.

SUMMARY OF THE INVENTION

One aim of the present invention is to provide a method of constructing internal standards for accurately quantitating levels of specific RNA and DNA species by competitive polymerase chain reaction techniques.

In accordance with the present invention there is provided a method for constructing internal standards used in competitive polymerase chain reaction (PCR) for determining the amount of a target nucleic acid sequence in a sample, which comprises the steps of:

a) digesting the cloned target nucleic acid sequence with a cohesive-end generating restriction endonuclease;

b) filling the restriction endonuclease cohesive ends of step a) by Klenow fragment of DNA polymerase; and c) blunt-end ligating the fragment of nucleic acid of step b) to form the internal standard;
wherein the internal standard nucleic acid sequence differs from the target nucleic acid sequence such that a restriction endonuclease recognition site is destroyed by adding sufficient contiguous bases to the target nucleic acid sequence such that the size difference between the target nucleic acid sequence and the internal standard nucleic acid sequence can be detected by gel electrophoresis.

The preferred nucleic acid sequence used in accordance with the method of the present invention is DNA, RNA or mRNA.

The preferred nucleic acid sequence used in accordance with the method of the present invention is that of γ-actin.

In accordance with the present invention, the following terms are defined as follows.

"Complementary DNA" or a "cDNA" as used herein includes recombinant genes synthesized by reverse transcription of mRNA and from which intervening sequences (introns) have been removed.

"Template" as used herein refers to a nucleic acid polymer, such as DNA or RNA, which is capable of serving as a substrate for the enzymatic polymerization of a complementary nucleic acid strand. A "competitive" template as used herein refers to a template which utilizes identical primers for PCR amplification as that of a "target" template but which differs from the target template in a manner which is detectable, for example, by a mutation, insertion or deletion of a portion of the sequence of the target template. As used herein, the "competitive" template is the standard's template and the "target" template is the template of the unknown whose levels it is desired to determine using the methods of the invention.

"Primer" as used herein refers to an oligonucleotide preferably an oligodeoxynucleotide, which possesses a free 3'OH group which, upon hybridization to a nucleic acid template, is recessed relative to the 3' end of the template and thus is capable of acting as a site of initiation of the synthesis or polymerization of a nucleic acid polymer, the sequence of which is complementary to the template strand, in the presence of deoxynucleotide substrates, an appropriate enzyme capable of DNA replication, and a suitable temperature and pH. Primers that consist of the same sequence are said to be 100% homologous. Primers that are non-homologous consist of completely different sequences. Various degrees of intermediate homology are possible, for example, 50% homology, greater than 50%, and less than 50%.

The primers and primer binding sites of the standard and target may consist of different lengths as long as, as discussed above, the primers and primer binding sites are functionally equivalent.

Such functionally identical primers and primer binding sites may also be used with competitive anchored PCR.

"Amplification" as used herein refers to an increase in the amount of the pre-existing nucleic acid template.

DETAILED DESCRIPTION OF THE INVENTION

Figure 1:
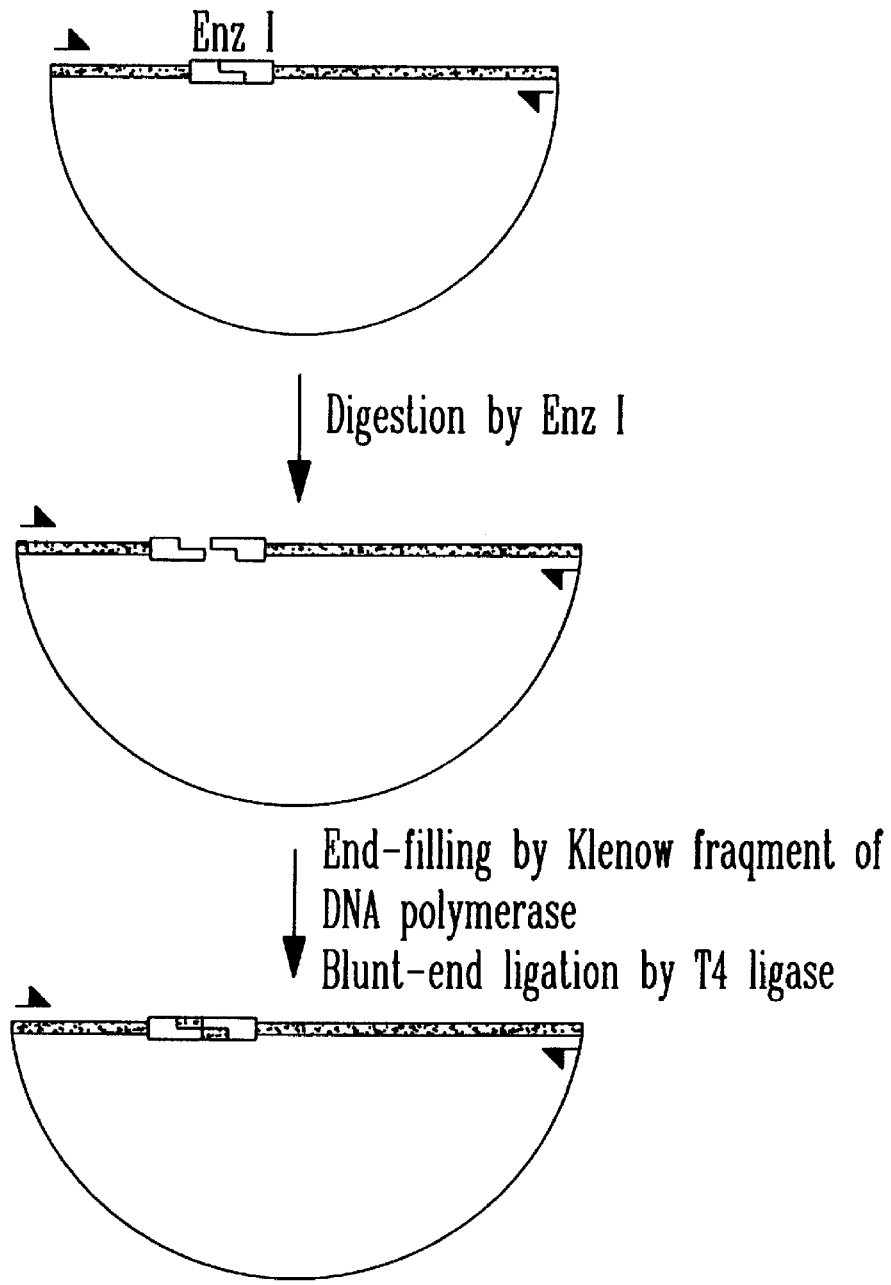
FIG. 1 is a schematic representation of internal standard generation through modification of a restriction endonuclease cut-site.

The method, outlined in FIG. 1, consists of two steps. A single cut restriction endonuclease is used to digest the plasmid containing the target sequence. The linear plasmid is end-filled using Klenow fragment of DNA polymerase and blunt-end ligated. The resulting circular plasmid has lost the restriction site and can be used as a competitor for quantitative PCR. On the first step, the target is cloned in a plasmid (for example: pBlueScript™ from Stratagene). A restriction map of the insert is obtained either from a suitable DNA analysis computer program if the target sequence is known, or from digestion of the insert with different restriction endonucleases. On the second step, a single site-cutting, cohesive end-generating restriction endonuclease is chosen, which is used to completely cut the insert. The resulting fragment is purified by a QIAquick™ spin column (QIAGEN), the cohesive ends are filled with Klenow fragment of DNA polymerase, and the blunt-ends are ligated by T4 ligase. The insert thus modified will loose a restriction site, and will become suitable to be used as a competitor in DNA/cDNA quantitative PCR.

Figures 2A, 2B:
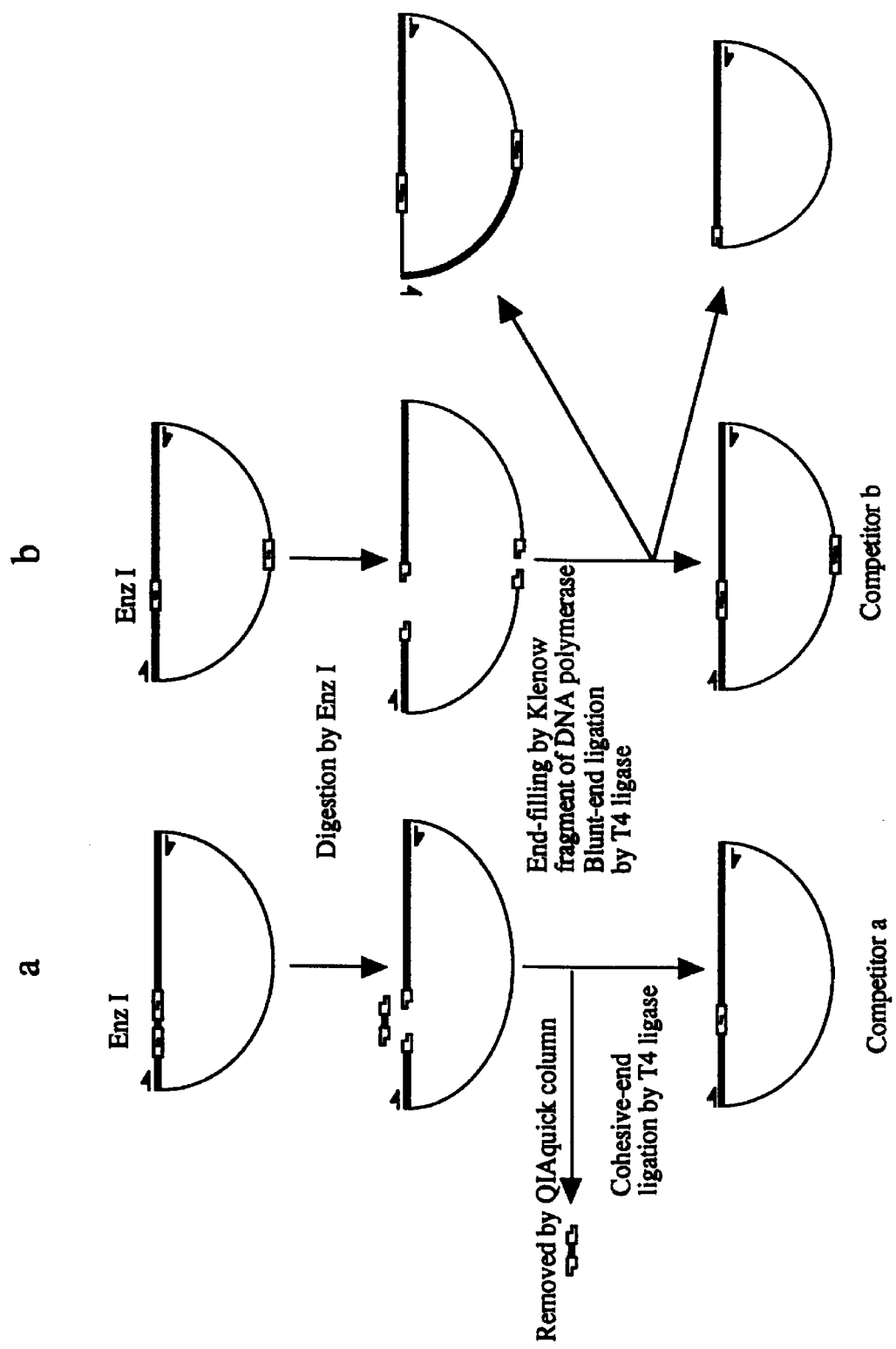
FIGS. 2A and 2B illustrate a schematic representation of internal standard generation by using a restriction endonuclease which cuts twice.

When no single site-cutting restriction endonuclease is available for the insert, a restriction endonuclease that cuts closely twice in the insert can also be used since the small fragment (<100 bp) generated by the two cuts will be removed by the QIAquick™ spin column. The resulting competitor will have a slightly smaller insert than the target, and the size difference between the competitor and the target will allow for direct comparison of the final PCR products without using a digestion procedure (FIG. 2A). A restriction endonuclease which cuts twice closely in the target sequence will release a short fragment (ideally not more than 10% of the target). The subsequent cohesive-end ligation will generate a novel plasmid construction with a shorter target (competitor a) which can serve as a competitor of PCR. Since the difference in size between the target and the competitor is small (10%), the unevenness of PCR amplification is negligible. If the selected restriction endonuclease cuts once in the insert and once in the plasmid, it is still possible to use it to make a valid competitor. As illustrated in FIG. 2B, all cohesive ends will be filled out and ligated. If the plasmid is also cut by the restriction endonuclease, a blunt-end ligation of all fragments will produce several recombinants but only the correct one is selected through PCR amplification (competitor b). This will result in three major types of construct but the correctly constructed competitor can be easily selected by PCR. Since numerous restriction endonucleases are available in the market, different strategies using the approach mentioned above could be easily designed for generating internal standards for competitive PCR in RNA/DNA quantification.

We have utilized this method to construct several competitors for quantitative PCR and found that the procedure is simple and cost effective.

The present invention will be more readily understood by referring to the following examples which are given to illustrate the invention rather than to limit its scope.

EXAMPLE I

γ-actin

Figure 3A:
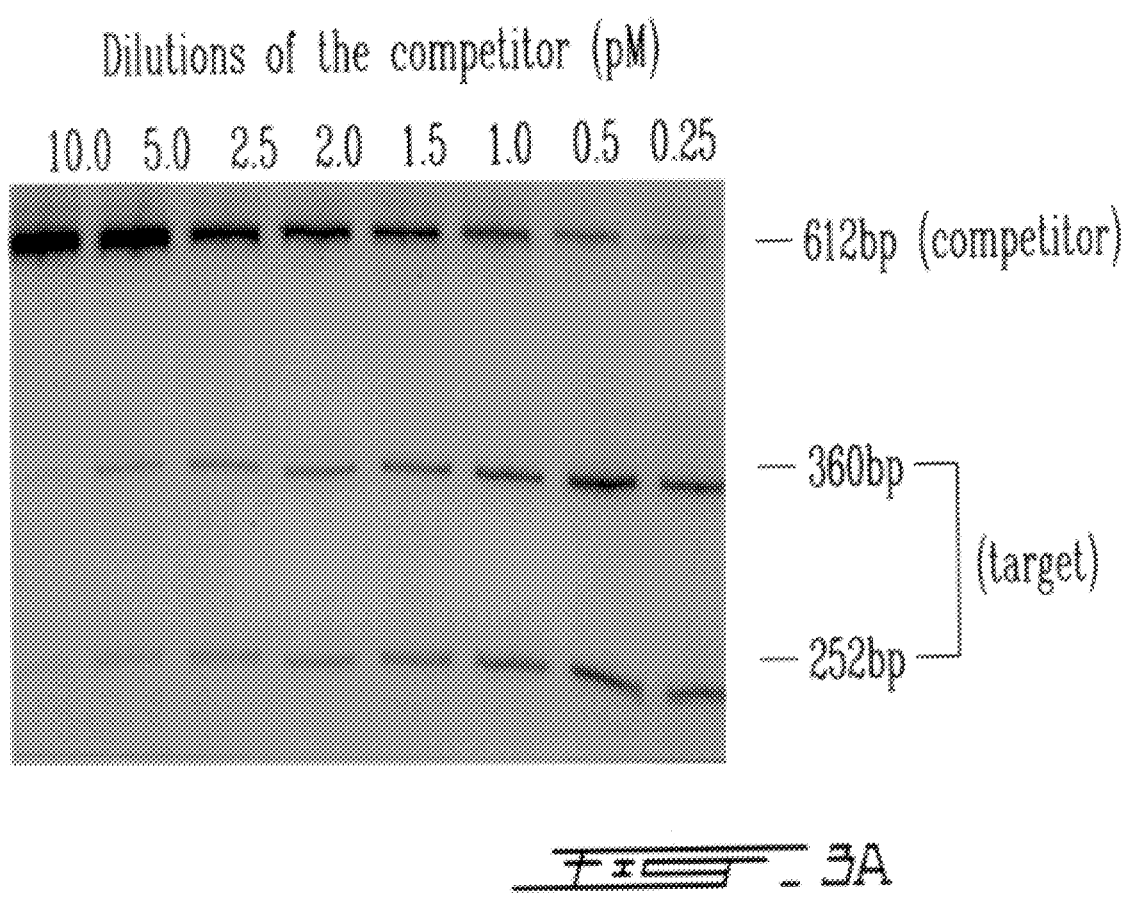
FIG. 3A illustrates a sample amplification of competitive PCR with a serial dilution of the internal standard and a fixed amount of target by autoradiography.
Figure 3B:
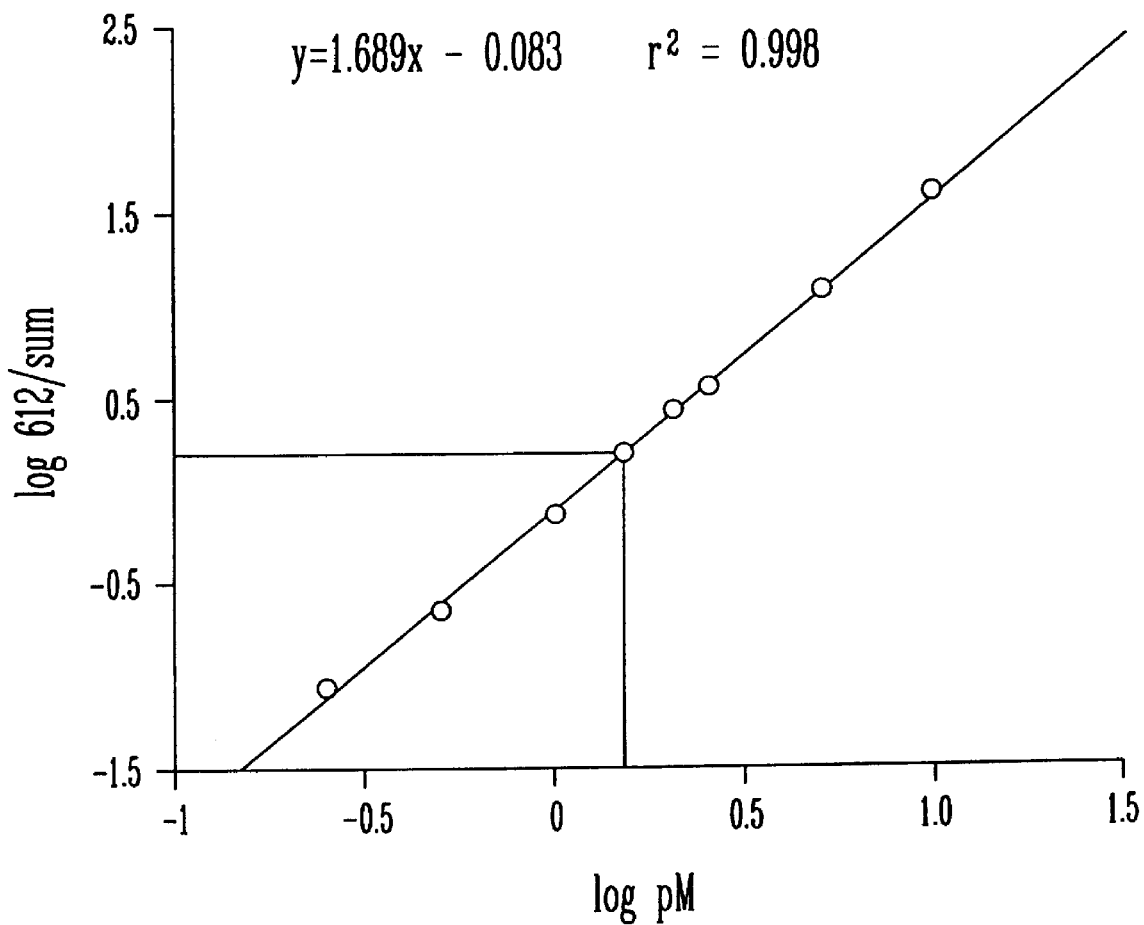
FIG. 3B is a graph of the sample linear amplification of competitive PCR.

A fragment of γ-actin CDNA was cloned into a plasmid vector. An internal standard of this γ-actin was generated by modifying the BstEII site which cuts γ-actin into two fragments. FIG. 3A shows a sample amplification of competitive PCR (with ½ incorporation of $\alpha^{32}$ P-dATP) with a serial dilution of the internal standard and a fixed amount of target, as visualized by autoradiography. The same gel was processed by PhosphorImager SI™ and the digital quantification was calculated by Image QuaNT™ software. As shown in FIG. 3B, linear amplification has been achieved. The products amplified from the internal standard decreased, while those from the target increased with the dilution of the internal standard. The quantity of internal standard used to achieve equal amplification of target DNA is interpreted as the quantity of the target.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method for constructing internal standards used in competitive polymerase chain reaction (PCR) for determining the amount of a target nucleic acid sequence in a sample, said method comprising:
   a) digesting the target nucleic acid sequence, which has been cloned into a plasmid vector with a cohesive-end generating restriction endonuclease to form a linear fragment;
   b) filling said restriction endonucleage cohesive-ends of step a) by Klenow fragment of DNA polymerase; and
   c) blunt-end ligating the fragment of nucleic acid of step b) to recircularize the plasmid and form said internal standard;

wherein said internal standard nucleic acid sequence differs from said target nucleic acid sequence such that a restriction endonuclease recognition site is destroyed and the size difference between said target nucleic acid sequence and said internal standard nucleic acid sequence can be detected by gel electrophoresis.

2. The method of claim 1, wherein said nucleic acid sequence is DNA.

3. The method of claim 1, wherein said nucleic acid sequence is RNA.

4. The method of claim 3, wherein said RNA is mRNA.

5. The method of claim 4, wherein said standard nucleic acid is γ-actin.

* * * * *